United States Patent [19]
Pratt et al.
[11] 4,107,283
[45] Aug. 15, 1978

[54] TRACER FOR CIRCULATION DETERMINATIONS

[75] Inventors: Frederick P. Pratt, East Somerville; David L. Gagnon, North Billerica, both of Mass.

[73] Assignee: New England Nuclear Corporation, Boston, Mass.

[21] Appl. No.: 706,434

[22] Filed: Jul. 19, 1976

[51] Int. Cl.[2] ...................... A61K 29/00; A61K 43/00
[52] U.S. Cl. ........................................ 424/1; 250/303; 252/301.1 R; 264/0.5
[58] Field of Search ........................ 424/1, 9; 250/303; 252/301.1 R; 264/0.5; 423/2; 427/6, 2, 5, 8

[56] References Cited

U.S. PATENT DOCUMENTS

| | | | |
|---|---|---|---|
| Re. 29,066 | 12/1976 | Evans | 424/1 |
| 4,010,250 | 3/1977 | Parikh et al. | 424/1 |
| 4,021,364 | 5/1977 | Speiser et al. | 424/1 |

*Primary Examiner*—Benjamin R. Padgett
*Assistant Examiner*—Christine M. Nucker
*Attorney, Agent, or Firm*—Sewall P. Bronstein

[57] ABSTRACT

A tracer comprising a polymer coated ion exchange core either labelled with nuclide, stable or radioactive or unlabelled and finding particular utility in circulatory determinations in animals or in the chemical process industries to detect or measure fluid flow.

40 Claims, No Drawings

TRACER FOR CIRCULATION DETERMINATIONS

BACKGROUND OF THE DISCLOSURE

Various methods for producing particles carrying radioactive nuclides are known. One method, disclosed in U.S. Pat. No. 3,334,050, comprises the application of high temperatures for sealing nuclides into the interstices of ion exchange cores by carbonizing the core.

This method has certain liabilities in that it is difficult to obtain a high yield of uniform and desired size cores because of the difficulty in controlling shrinkage of the particles. In addition, certain nuclides such as $^{203}$Mercury or $^{125}$Iodine are extremely volatile at temperatures used for carbonization and thus losses of these nuclides would be expected to occur. Furthermore, it has been found in practice that particles produced in this manner when utilized as an injectable preparation in animal research tend to agglomerate both in an injectable preparation and in vivo thus comprising test results.

Another technique which is set forth in U.S. Pat. No. 3,492,147 relys upon use of a non-reactive or inert substrate (e.g., sand, glass, etc.) to which a monomeric coating containing radioactive nuclides is applied and is polymerized by extraction of a catalyst from an acid bath which is contacted with monomer coated particles. It has been found in practice that with this process substantial undesired bulk polymerization occurs, which limits the usefulness of the product.

A further process of the prior art involves the incorporation of $^{51}$Cr acetylacetonate (a chelating agent) into polystyrene and polystyrene vinyl latices in toluene (non ion exchange resin) by a process called emulsion polymerization. This process tends to produce particles of very small dimensions (about 0.1 to 1.5 microns) which are too small for convenient use in animal circulatory studies.

In view of the foregoing, a new and improved product and method was needed for providing a tracer particle having an ion exchange resin core with a controlled thickness polymer coating. In particular the process of this invention has significant advantages over the prior art in that a uniform coating may be obtained in a short period of time (less than 3 hours) merely using a vessel containing the monomer and the cores having catalyst incorporated thereon. The ion exchange particles lend themselves ideally for incorporation of a large variety of different types of nuclides and in addition also provide advantage in that they are capable of being readily conditioned with catalyst ($H^+$ or $OH^-$ depending on the monomer used) to effectuate the formation of a substantially non-leaching controllable thickness coating on the surface of the cores. As used herein the term leaching refers to the leaching of ions from the ion exchanger resin core through the coating. Applicants on the other hand have found that an inert particle such as sand does not have these properties and applicants were not able to produce a satisfactory coating using the same process as performed by them with the ion exchange resin.

The product of this invention has also unexpectedly been found to be non agglomerating in an injectable suspension, and when used in vivo or when stored in dry form.

BRIEF STATEMENT OF THIS DISCLOSURE

This invention is directed to a new and improved tracer particle having a polymeric coating on an ion exchange core and the process of preparing same. It has been found in this invention that a tracer particle either incorporating or not incorporating nuclides e.g., radionuclides, may be readily provided with a substantially non-leaching protective polymeric coating by the contacting of an ion exchange core possessing catalytic sites with an acid or base catalyzed monomer or monomers depending upon the type of catalytic site, i.e., an acid catalyzed monomer(s) is used when the catalytic sites bear $H+$ ions and a base catalyzed monomer(s) is used when these catalytic sites possess $OH^-$ ions. The tracer particles of this invention are useful in circulatory determinations involving the injection of the particles as a suspension in a physiologically acceptable carrier or medium into the circulatory system of animals.

The animals are normally sacrificed to permit the determination of the distribution of particles throughout the body. The determination of the distribution of particles throughout the body may be made by visual microscopic examination after sacrifice of the animal, by the use of conventional radioactivity counters when radioactive ions are incorporated in the particle or by conventional x-ray fluorescence techniques where the ions are stable nuclides and excited by x-rays to emit characteristic radiation.

This determination is useful to clinical and medical investigators as a tool for determining blood flow and the affect of drugs, e.g., vasodilators and vasoconstrictors in blood flow. In addition, the tracer particles of this invention may be introduced into process control streams found in the chemical industry to determine the flow of fluid in the stream, e.g. by the making of radioactivity measurements along the length of the stream. The ion exchange cores which can be used in the invention are anionic or cationic organic ion exchange resin cores or inorganic ion exchange cores. Many such ion exchange cores are known, and it is well known that they can be obtained in forms which will permit exchange with particular ions, or can be placed in such form by treatment with the proper reagent.

Examples of the useful organic ion exchange resin cores include the strongly acidic sulfonated polystyrene resins, phenolic resins containing methylene group linked sulfonic groups, polystyrene resins containing phosphonic groups, acrylic resins containing carboxylic groups, polystyrene resins containing quarternary ammonium groups, pyridinium group substituted polystyrene resins, epoxypolyamine resins containing tertiary and quarternary ammonium groups, polystyrenes containing weakly acidic iminodiacetic groups and polystyrene resins containing polyamine groups. Also included are inorganic ion exchange cores such as aluminum oxide, zirconium phosphate, zirconium tungstate, zirconium molybdate, zirconium oxide, magnesium dioxide and others as set forth in an article by Girardi, et al, in the Journal of Radioanalytical Chemistry, Vol. 5 (1970) P. 141–171. These cores are available in particulate form such as tiny spherules having diameters of the order of 10 to 200 microns and irregularly shaped particles. Any of such forms can be employed in the process of the invention; and while there are no limitations on the size of particles which can be employed herein, preferably spherical beads or irregular particles of a size of the order or about 10 to 200 microns diameter or maximum dimension are employed. Larger particles can be used for particular, specific purposes; however, as a practical matter the particle size is kept to that which passes through a 50 mesh screen, i.e., about 200 microns. For medical diagnostic or therapeutic purposes, the particles are preferably spherical to prevent unintentional passage of the particles into smaller than intended blood vessels and furthermore, limited to preselected sizes and size distribution.

In animal circulatory studies, the cores preferably have a density between 1 to 1.5 and most preferably about a density of about 1.1 to 1.3 which is close to the density of blood. Broadly speaking, any element radioactive or non-radioactive which is capable of existing as an ion in solution can be employed in this invention.

Particularly useful radioactive ions are $Cerium^{141}$, $Chromium^{51}$, $Strontium^{85}$, $Scandium^{46}$ and others well known in the art. With anionic resins, the radionuclides are in the form of anions, e.g., radioactive pertechnetate, chromate or other complex negative acid radicals containing the aforementioned radionuclides and others. Generally speaking, the ion exchange core in practice would preferably have adsorbed thereon 0.1 to 100 millicuries per gram of core when a radionuclide ion is employed, although other ranges of radioactivity may be used depending upon the application. See Helfferich F. *ION EXCHANGE,* McGraw-Hill Book Company, New York (1962) or other techniques such as shown in U.S. Pat. No. 3,334,050. Non-radioactive nuclides such as strontium, barium, iron, zinc, etc., are also adsorbed on the cores.

The cores of this invention are preferably labelled with the aforementioned radionuclide ions using conventional batch ion exchange techniques well known in the art. The radioactive ion is chemically bonded to the resin which therefore increases its resistance to being leached out.

The polymeric process for the preparation of the coated tracer of this invention broadly comprises contacting a monomer with cores bearing caralytic ions (hydroxyl or hydrogen) on the surface thereof which are present in an amount sufficient to catalyze the monomer. As used herein the term monomer is meant to include one or more monomers which react to form a polymer or copolymer.

The cores are preferably reacted batchwise with monomer to provide the individual or monodispersed coated tracers.

Unexpectedly in all cases, no, or very little, polymerization occurs in the bulk of the monomer solution, even through polymerization is extensive and complete on the core surface. In every case, after the coated particles or tracers are separated from the remaining monomer and partially polymerized polymer, and then rinsed and dried, they are free flowing and monodisperse. It is to be emphasized that no lubricants, oils, resins or waxes are required to prevent the individual particles from adhering to one another or each other; it is believed the unique approach of selectively incorporating the catalyst on the surface of the particles results in this desirable characteristic, regardless of the particular monomer employed. It is also to be emphasized that no further treatment is necessary in order to effect a hard, uniform, impermeable and non leaching coating on the particles, although with some monomers, the coating can be desirably further cured by heating in an oven at 60° to 110° C for an appropriate period of time, e.g., 1 to 20 hours.

The monomers which are used in the practice of this invention are those which are either base or acid catalyzed. The preferred monomer for this invention is furfuryl alcohol.

Other monomers and monomer mixtures useful in this invention, include furfuryl alcohol- formaldehyde, furfural, phenol-formaldehyde, phenol-furfural, phenol-furfuryl alcohol, furfural-acetone, urea-formaldehyde, urea-formaldehyde-furfuryl alcohol, furfural-furfuryl alcohol-phenol, analine-furfural, melamine-formaldehyde, tetrahydrofurfural alcohol and melamine-furfural. In addition, other acid and base catalyzed monomer and monomer systems such as those described in the *Encyclopedia of Polymer Science and Technology,* (1965), published by John Wiley Co. (1st. Edition). may also be used as would be apparent to those skilled in the art.

In addition, it is also useful in the aforementioned cases, to employ partially polymerized monomer or monomer mixtures in order to achieve extensive and complete polymeric coatings. For example, partially polymerized furfuryl alcohol which can be obtained commercially from HOOKER CHEMICAL COMPANY, DUREZ DIVISION, can also be utilized to apply an effective coating to the particular cores.

In the practice of this invention, it is preferable that in order to obtain a substantially non-leachable coating, the coating thickness should be greater than 0.5 microns. In order to achieve this, the ratio of weight of ion exchange core to the weight of monomer is preferably one part ion exchange core to a range of 0.5 to 20 parts by weight of monomer. In practice, the most preferred range of application of furfuryl alcohol as furan polymeric coating is one part by weight ion exchange core to a range of 2 to 10 parts by weight of furfuryl alcohol.

These conditions lead to coatings which range from about 0.5 microns to 5 microns in thickness, and preferably range from one to three microns in thickness.

The catalytic ions, i.e., $H^+$ or $OH^-$ for initiating polymerization of the monomer depending on the type of monomer i.e., whether it be the type of monomer which is base or acid catalyzed, are normally incorporated in the commercially available ion exchange resins as purchased. Alternatively the ions may be applied to ion exchange cores by immersing same in HCl, dilute $H_2SO_4$, dilute $HNO_3$, NaOH, KOH, $NH_4OH$ or any other acids or bases conventionally used for this purpose in the art. Preferably, for the process of this invention, the ion exchange cores contain from 1.5 to 5 millequivalents of $H+$ per gram of ion exchange cores in the case of cation catalyzed monomers, and about 0.5 to 3 millequivalents of $OH^-$ per gram of anion catalyzed monomers.

In essence, in accordance with the invention the acidity or basicity, i.e. $H^+$ or $OH^-$ ions, whichever the case may be, at the surfaces of the cationic or anionic exchange material, is relied on for selective catalytic polymerization of the monomer at such surfaces. Accordingly, during the step of ion exchange of radioactive cations or anions for the ions of the ion exchange resin, sufficient residual $H^+$ or $OH^-$ ions should remain to catalyze polymerization at the resin surface. The amount of residual $H^+$ or $OH^-$ ions in the resin can be controlled by controlling the amount of radioactive cations or anions in the resin and by exchanging remaining $H^+$ or $OH^-$ ions for non acidic cations, e.g., sodium, or non basic anions.

It is intended that the ions used to catalyze the coating reaction, $H^+$ or $OH^-$, include those substances which simulate those ions in their catalytic effect. The catalyzed coating reactions herein are exothermic and are conducted at room temperature, although heat may be applied to the monomer reaction mixture to increase labeled with 100 millicuries $^{141}Ce$ by the loading technique described in Example #2 was mixed with 10 ml furfuryl alcohol. Constant stirring and application of moderate heat resulted in a vigorously exothermic reaction. After the reaction subsided and cooled, the coated resin beads were filtered off and washed with acetone and dried. The coated resin beads were observed to be black and monodispersed. The coating was ascertained to be impervious to acids and water by washing a column containing 33 mCi of the coated resin beads with 0.1% Tween 80 solution, then 2N, 6N, and 9N HCl, successively. The percent of loaded activity leached off was respectively 0.00%, 0.23%, 0.05%, 0.02%. By comparison of the activity per unit weight of resin beads before and after coating, the coating was found to have resulted in a weight gain of 256%. In vivo testing in mice indicated no significant leaching of activity after 48 hours. Microscopic examination indicated all beads to be smoothly and uniformly coated with no extraneous polymer particles present and possessing a mean diameter of 23.9 ± 2 micrometers.

EXAMPLE #4

3.7 grams of anion exchange resin cores, strongly basic, styrene type containing quarternary amine groups in hydroxyl form, of size 20–50 mesh (AG1-x8) Bio-Rad was mixed with a solution of 5 ml furfural and 5 ml acetone and stirred continuously. The mixture was placed in a water bath and the temperature slowly increased to 70° C, then allowed to cool. The coated product was then filtered and washed with acetone. The product was then dried and cured at 55° C for 18 hours.

The coated product consisted of brown, monodispersed particles. A total weight increase of approximately 4% was realized.

EXAMPLE #5

3.9 grams of a strongly acidic cation exchange resin cores of a sulfonated polystyrene type of size 200–400 mesh (AG50W - X8), Bio-Rad, mixed with a solution of 5 grams of phenol dissolved in 10 ml formaldehyde and stirred constantly. The mixture was placed in a water bath and the temperature slowly increased to 80° C, then the reaction mixture allowed to cool. The product was filtered and washed with acetone. At this point the product consisted of red, monodispersed particles.

The product was then dried and cured at 110° C for 18 hours. The resulting product consisted of black monodispersed particles.

EXAMPLE #6

To demonstrate control of the final product, batches of various weights of strongly acidic cation exchange resin cores in the $H^+$ form (200–400 mesh) AG50W-x8 were reacted, each with 5 ml of furfuryl alcohol (F.A.) and coated. The reaction mixtures were mixed continuously and underwent spontaneous reactions to attain the final coated products. In each case the product was washed with acetone and then dried at 110° C for 18 hours. The following table demonstrates the controllable aspects of the process.

TABLE I

REACTION CONTROL BY VARIATION OF FURFURYL ALCOHOL/RESIN RATIO

| Amt. of F.A. | Total Wt. of All Resin Particles | Max. Temp. of Reaction | Time to Attain Max. Temps. | Wt. Increase |
|---|---|---|---|---|
| 5 ml | 0.5 g | 28° C | 204 sec. | 76% |
| 5 ml | 1 g | 24° C | 368 sec. | 93% |
| 5 ml | 2 g | 69° C | 533 sec. | 153% |
| 5 ml | 3 g | 98° C | 451 sec. | 138% |

Additionally, control of the reaction and the product can be attained by varying the amount of acid incorporated into the resin (i.e., the $H^+$ concentration of the resin). Table II demonstrates this aspect in each case in which approximately 2 grams of resin cores as above were reacted with 5 ml of furfuryl alcohol. With continuous mixing, a spontaneous reaction occurred in most cases. The product was washed with acetone and dried and cured at 110° C for 18 hours. The first example, run with resin in the $NA^{30}$ form ($_{No\ H+}$) demonstrates clearly the affect of incorporating catalyst in or onto the resin particles.

TABLE II

REACTION CONTROL BY VARIATION OF FURFURYL ALCOHOL/ACID RATIO

| Total $H^+$ Incorporated into the particles | Max. Temp. of Reaction | Time to Attain Max. Temp. | Wt. Increase |
|---|---|---|---|
| 0 meq | No reaction occurred* | | — |
| 1 meq | 24° C | 900 sec. | 22% |
| 2 meq | 29° C | 1050 sec. | 47% |
| 3 meq | 37° C | 1025 sec. | 74% |
| 4 meq | 52° C | 900 sec. | 114% |
| 5 meq | 68° C | 533 sec. | 153% |
| 6 meq | 98° C | 451 sec. | 138% |

meq=milliequivalents of total hydrogen ion (H +).
*This example, conducted with the above mentioned resin in the Na+ form, gave no evidence of a reaction; i.e. there was no temperature change or no change in color of the resin particles. Ambient temperature was 21° C during these experiments.

EXAMPLE #7

2 grams of strongly acidic cation exchange resin cores of a sulfonated polystyrene type in the $H^+$ form of size 200–400 mesh (as in Example 6) was mixed with a solution of 2 grams urea dissolved in 5 ml formaldehyde and the mixture stirred constantly. An immediate spontaneous reaction occurred with a temperature increase to 40° C in 85 seconds. The resulting white product was filtered, washed in acetone then dried and cured at 110° C for 18 hours.

The resulting product consisted of spherical resin particles with a white coating of urea formaldehyde polymer.

EXAMPLE #8

4 grams of strongly acidic cation exchange resin cores of a sulfonated polystyrene type in the $H^+$ form of size 200–400 mesh (as in Example 6) was mixed with a solution of 10 ml furfuryl alcohol and 10 ml formaldehyde and stirred constantly. An immediate reaction occurred with a temperature increase to 64° C in 950 seconds, and a darkening of the reaction mixture. The product was filtered, washed with acetone, then dried and cured at 110° C for 18 hours.

The resulting product consisted of black, spherical, monodispersed particles, exhibiting a weight increase of 110%.

the polymerization rate to provide the coating on the cores.

A solvent such as water (moisture) which causes the localized disassociation of the $H^+$ or $OH^-$ ions as the case may be is required in the system to permit catalysis by making the catalytic ions available to the monomer. To accomplish the ions exchange cores may contain water. The amount of water depends upon the particular ion exchange material and is easily determined by routine testing by those skilled in the art.

There should be enough so that sufficient catalysis is achieved to provide a good coating of polymer but there should not be so much that the $H^+$ or $OH^-$ ions become too dilute or that the monomer solution is rendered too dilute.

A range of water content is between 10 to 90% and preferably 45% and 65% of the weight of the ion exchange material. The most preferred water content in most cases is equilibrium moisture content at ambient conditions.

Monomer systems containing water may be used in lieu of the above to accomplish catalysis of the monomer.

The following examples illustrate the invention. Except where otherwise noted all procedures in the examples were initiated at room temperature (17° - 22° C).

EXAMPLE #1

2.5 grams, containing 57.8% moisture, of a strongly acidic cation exchange resin of the sulfonated styrene type (obtained from Bio-Rad Laboratories, Richmond, California, Type Aminex A-5) in the form of 10-15 micron diameter spherical particles (cores) was mixed with a 10-mls of a solution of 4.6 millicures $^{85}Sr$ as the chloride salt in 2N HCl. The solution was diluted until the acid concentration was approximately 0.2N HCl. The resin cores were then filtered and the filtrate assayed with a conventional ion chamber device, which indicated that 98% of the total activity was incorporated into the resin. The resin was then oven dried at 100° C for 30 minutes to approximately 57% moisture content. 1.4 grams of this nuclide labelled resin was then mixed with 10 mls of furfuryl alcohol with constant mixing. A spontaneous immediate reaction occurred which caused the temperature of the reaction mixture to increase from room temperature to 101° C over a time span of 195 seconds. After the temperature peaked and started to decrease, the coated product was filtered and washed with acetone. The product was then dried at 110° C for 18 hours.

The resultant product was composed of black monodispersed spherical particles. The final weight of the product was 2.1 grams with a specific activity of 1.2 millicuries per gram.

Impermeability of the coating was tested by passing a solution of 2N HCl through a bed of the product and also by passing physiological saline (0.9% NaCl solution) through the bed. In both cases, only 0.1% of the loaded activity was leached from the coated resin beads. Additionally, storage of the product in 0.9% NaCl solution for a period of 25 days resulted in leaching of not more than 1% of the activity.

In addition, in vivo animal tests of the material demonstrated that no significant leaching of activity or breakdown of particles occurred within the 24 hour time span of the test.

Microscopic examination of the product indicated the particles were spherical and exhibited a means diameter of 16.1 ± 0.9 micrometers compared to a mean diameter for the uncoated resin of 14.3 ± 1.0 micrometers (microns), and moreover, the narrow size distribution of the particles was completely retained.

EXAMPLE #2

1.6 grams (dry weight) $H^+$ cation resin core of a nominal 15 micrometer diameter (Aminex A-5) was uniformly loaded with 104 millicuries of $^{51}Cr$, by diluting the acid supernate from 2N to 0.02N $H^+$ concentration. After loading, the supernate was removed, and the resin cores were slurried with a small volume of water to facilitate transfer to a 250 ml Florence flask, to which 10 ml of furfuryl alcohol was added followed by constant stirring and a small amount of heat. A vigorous exothermic reaction ensued, the reaction mixture becoming black and viscous. When the reaction had subsided and cooled, the coated resin beads were filtered off and washed with acetone. The resin beads appeared black and monodispersed. The reaction filtrate contained 0.022% of the loaded activity while the acetone wash contained only $2.5 \times 10^{-4}$% of the loaded activity. The impermeability of the coating was ascertained by loading the entire batch into a column and washing by gravity flow at a flow rate less than 1 ml/minute with various reagents in the sequence listed. The percent of activity removed from the coated resin particles is shown in the table below.

| Reagent | Volume | % of $^{51}Cr$ Activity Removed |
|---|---|---|
| 0.1% Tween 80 | 10 ml | 0.004 |
| 2N HCl | 10 ml | 0.61 |
| $H_2O$ | 10 ml | 0.008 |
| 2N HCl | 10 ml | 0.05 |
| $H_2O$ | 10 ml | 0.02 |

Comparison of activity per unit weight of product before and after coating indicates a weight gain due to coating of 270%. Integrity of coating is maintained even after oven drying at 140° C for 24 hours as evidenced by another 10 ml 2N HCl leach of just 0.13% of the activity in the particles. Integrity of coating continued to be maintained after dry storage for 1 month followed by wet storage in various solutions for 10 days. Percentages of activity that leached from the coated particles after storage were: 0.003% for $H_2O$ or 0.1% Tween 80, 0.5% for 2N HCl, and 0.2% for 0.9% bacteriostatic NaCl solution.

Microscopic examination showed black, completely coated, monodispersed unbroken resin beads having an increase in the mean diameter of 2.9 micrometers, from 12.3 ± 0.9 to 15.2 ± 1.5 micrometers. No extraneous pieces of polymer could be found. Microscopic examination of the oven dried coated resin beads (140° C for 24 hours) showed no change in the mean diameter as a result of drying.

Measurement of activity on weighed samples of various sizes indicates that activity is uniformly distributed within ± 5%.

Animal studies conducted over a period of up to 8 days indicated little leaching of the $Chromium^{51}$ activity from the injected particles, again demonstrating integrity of the furan coating on these particles.

EXAMPLE #3

2.0 grams (dry weight) of $H^+$ form cation resin cores of 20.3 ± 1.9 micrometers diameter (Aminex Q-15S)

EXAMPLE #9

4 grams of strongly acidic cation exchange resin cores of a sulfonated polystyrene type in the $H^+$ form of size 200–400 mesh (as in Example 6), was mixed with 5 grams of phenol and 5 ml of furfural and stirred constantly. The mixture was placed into a water bath and the temperature slowly increased to 80° C. The mixture was then allowed to cool, was filtered, washed with acetone, then dried and cured at 110° C for 18 hours.

The final product consisted of black monodispersed spherical particles and exhibited a weight increase of approximately 14%.

EXAMPLE #10

4 grams of 20 to 50 mesh (same as in Example #4) strongly basic anion exchange resin cores of polystyrene type in the OH− form, containing quaternary amine groups was mixed with 10 ml furfural and stirred continuously. The mixture was placed in a water bath and the temperature slowly increased to 60° C. The mixture was then cooled, filtered, washed with acetone and dried at 55° C for 18 hours.

The final product consisted of black, monodispersed spherical particles exhibiting a weight gain of approximately 24%.

EXAMPLE #11

2.6 grams of strongly acidic cation exchange resin cores of a sulfonated polystyrene type in the $NA^+$ form of size 200–400 mesh (same as in Example 6) was conditioned by treating with 2 ml of 2.5N NaOH and drying at 110° C for 15 minutes. The NaOH was not washed out of the resin and thus was incorporated onto the resin particles. The conditioned resin was then mixed with a solution of 5 ml furfural and 5 ml acetone and stirred constantly. An immediate spontaneous reaction occurred with the temperature increasing to 60° C in 96 seconds. The mixture was allowed to cool, then filtered, washed, dried and cured at 110° C for 18 hours.

The resulting product consisted of black monodispersed spherical particles and exhibited a net weight increase of approximately 26%.

EXAMPLE #12

2.7 grams of strongly acidic cation exchange resin cores of a sulfonated polystyrene type in the Na+ form and size 200–400 mesh (same as in Example 6) was conditioned by treating with 2 ml of 2.5N NaOH and drying at 110° C for 15 minutes. The NaOH was not washed from the resin and thus was incorporated onto the resin particles. The conditioned resin was mixed with 10 ml of furfural and mixed constantly. An immediate mild reaction occurred with the temperature of the mixture rising to 27° C in 200 seconds. The product was filtered, washed with acetone then dried and cured at 110° C for 18 hours.

The resulting product consisted of brown, monodispersed spherical particles, and exhibited a net weight increase of approximately 32%.

EXAMPLE #13

5 grams of strongly acidic cation exchange resin cores of the sulfonated styrene type (Q15-S) BIORAD containing 57% moisture, and of size 22 microns diameter were mixed with 50 ml of furfuryl alcohol, and stirred constantly.

An immediate, spontaneous, reaction occured which caused the temperature of the reaction mixture to increase to 106° C in a time span of 110 seconds.

After the mixture cooled it was filtered and washed with 200 mls acetone, then dried at 110° C for 18 hours.

The resultant product consisted of black monodispersed particles. The size of the particles was 24 ± 2 microns.

EXAMPLE #14

Injectable Preparation

An injectable preparation was prepared by:

(1) Suspending 1 mCi (100 mg) of the particles of Example #3 in 20 ml of 10% Dextran solution with a trace amount of Tween 80 surfactant added to insure dispersion of the particles. The resulting suspension was ultrasonicated for approximately 30 minutes to provide uniform dispersion this point the suspension was at a concentration of 5 milligrams/milliliter and 0.05 millicuries/milliliter.

A typical injection of 20–25 microcuries was obtained by withdrawing approximately 0.5 ml of the suspension, containing approximately 2.5 mg of material or approximately $2\times10^5$ particles.

EXAMPLE #15

Injectable Preparation

An injectable preparation was prepared by:

(2) Suspending 1 millicurie (100 mg) of the particles of Example #3 in 10 ml isotonic saline with a trace of Tween 80 surfactant added to insure dispersion of the particles. The resulting suspension was ultrasonicated for 30 minutes to provide uniform dispersion. At this point the suspension was at a concentration of 10 milligrams per milliliter and 0.1 millicuries/milliliter.

A typical injection of 20–25 microcuries was obtained by withdrawing approximately 0.25 ml of the suspension containing approximately 2.5 mg of material or approximately $2\times10^5$ particles.

EXAMPLE #16

In order to determine blood flow to the oral tissues and brain of a 10.0 kilogram dog, a suspension of approximately six million 15 micron beads (approximately 20 microcuries) prepared as in Example #1 and labeled with $^{57}Co$, consisting of about thirteen milligrams of particles in six ml of 53% solution of sucrose in water was injected by arterial catheterization into the left ventrical of the animal. After about five minutes, the animal was sacrificed and all major organs as well as the brain and oral tissues were excised. Sections of each organ such as kidney, liver and lungs were used as internal controls and were counted with a gamma detector in order to determine flow to each organ. The oral tissues and brain were sectioned and also counted in order to determine the rate of blood flow in milliliters per minute per gram of tissue.

In addition, two arterial blood samples were withdrawn at a known rate from anterior and posterior blood vessels during injection in order to establish the random nature of the particle distribution in the circulatory system and allow for absolute calculation of blood flow and cardiac output.

It was established that bead uptake in brain and oral tissues correlated well with established baseline values for blood flow to these areas of the body.

Also, uptake in the other organs was representative of previously established values for flow to these organs.

Additionally, microscopic examination of the injected suspension showed that the microspheres were in a monodispersed state and that there was no evidence of clumping.

EXAMPLE #17

In an experiment to determine the cardiac output and blood flow to various organs in rats, a suspension of approximately 50,000 15 micron beads containing about 200,000 dpm of $^{85}Sr$ (approximately 0.1 microcurie (prepared as in Example 1)) in a volume of 0.25 ml of 63% sucrose was injected into the left ventricle of each of 5 rats. The suspension was prepared by adding 25 ml of 63% sucrose to about 5 million of the beads in the vial, ultrasonicating for 30 minutes, shaking and withdrawing 0.25 ml of the suspension into a syringe.

After a period of aproximately 30 seconds, the rats were sacrificed by an intravenous injection of saturated KCl and their hearts were excised, along with other organs, in order to determine the distribution of the microspheres in the animals. This was determined by counting of the organs in a gamma well counter coupled to a single channel analyzer. Results showed that the microspheres were situated where expected; i.e., they were located in areas of the rat organs where blood vessel cross sectional diameters were of the order of $15\pm2$ microns.

In order to determine whether the microspheres had remained monodispersed after injection while locating at the various sites, tissue specimens of the heart and other organs were examined with a microscope at 200–400 magnification. There was no sign of aggregation or clumping, since the beads were located individually in blood vessels of the same approximate diameter of the beads, and there was no evidence for beads locating in larger diameter blood vessels as would be the case for beads clumping together and representing a larger mass.

The values obtained for total cardiac output and for blood flow to several selected organs (spleen, liver, brain, gut, etc.) were in excellent agreement with values reported previously in the literature obtained with an equivalent product of different manufacture.

We claim:

1. An injectable preparation for use in making circulatory system measurements comprising ion exchange cores having a polymeric coating in a physiologically acceptable liquid carrier and a physiologically acceptable liquid carrier therefor.

2. The preparation of claim 1 in which the cores will pass through a 50 mesh screen.

3. The preparation of claim 2 in which the coating is of a thickness of 0.5 to 5 microns.

4. The preparation of claim 3 in which the coating is of a thickness of 1 to 3 microns.

5. The preparation of claim 1 in which the cores comprise ion exchange resin.

6. The preparation of claim 5 in which the cores are of a diameter of 10 to 200 microns.

7. The preparation of claim 1 in which radioactive ions are adsorbed on said cores.

8. The preparation of claim 7 in which the cores comprise ion exchange resin.

9. The preparation of claim 7 in which the radioactive ions are selected from the group consisting of $Cerium^{141}$, $Chromium^{51}$, $Strontium^{85}$, $Scandium^{46}$ and $Cobalt^{57}$ ions and the ion exchange resin is cation exchange resin.

10. The preparation of claim 1 in which the polymeric coating is a furan polymer.

11. The preparation of claim 9 in which the cores comprise ion exchange resin and the polymeric coating is a furan polymer.

12. A particle comprising an ion exchange core having a polymeric coating thereon.

13. The particle of claim 12 in which the core has radioactive ions chemically bonded thereto.

14. The particle of claim 13 in which the radioactive ions are selected from the group consisting of $Cerium^{141}$, $Chromium^{51}$, $Strontium^{85}$, $Scandium^{46}$ and $Cobalt^{57}$ ions.

15. The particle of claim 13 in which the core is an ion exchange resin.

16. The particle of claim 14 in which the core is a cation exchange resin.

17. The particle of claim 12 in which the core is of a size to pass through a 50 mesh screen and the coating is 0.5 to 5 microns in thickness.

18. The particle of claim 17 in which the coating is 1 to 3 microns in thickness.

19. The particle of claim 12 in which the polymeric coating comprises a furan polymer.

20. The particle of claim 12 in which the polymeric coating is the reaction product of a base or acid catalyzed monomer.

21. The particle of claim 20 in which the core is an ion exchange resin and has radioactive ions adsorbed thereon.

22. A method of making polymeric coated tracer particles comprising contacting a monomer selected from the group consisting of a monomer, the polymerization of which is catalyzed by $H+$ ions, and a monomer, the polymerization of which is catalyzed by $OH^-$ ions, with ion exchange cores having ions selected from the group consisting of $H+$ ions and $OH^-$ ions whereby polymerization of said monomer is catalyzed at the surfaces of said cores to form said coating.

23. The method of claim 22 in which the cores comprise ion exchange resins.

24. The method of claim 22 in which the cores have radioactive ions adsorbed on said cores.

25. A method of making tracer particles comprising polymerizing a monomer on the surface of radioactive labelled ion exchange cores which surface is catalytic to said polymerization, to form a polymer coating on said cores.

26. The method of claim 25 in which said polymerization is catalyzed by an acid or base and in which the surface has either acidic or basic catalytic sites depending on whether the polymerization is acidically or basically catalyzed.

27. The method of claim 26 in which the said catalytic sites comprise either $H+$ or $OH^-$ ions of the ion exchange cores depending on whether the polymerization is acidically or basically catalyzed.

28. A method of determining the characteristics of a circulatory system which comprises introducing into said system particles comprising a radioactive ion exchange core having a polymeric coating and determining the flow of particles in the system at a position removed from the introduction of said particles.

29. The method of claim 28 in which cores comprise ion exchange resin having radioactive ions adsorbed thereon.

30. The method of claim 29 in which the particles are injected into the circulation system of an animal.

31. The method of claim 28 in which the number of labelled particles is determined by counting the amount of radioactivity.

32. A tracer particle comprising an ion exchange core incorporating radioactive ions and a polymeric coating over said core of a thickness sufficient to prevent substantial leaching of the ions from the particles.

33. The tracer according to claim 32 in which the coating is a polymer of a monomer selected from the group consisting of a monomer, the polymerization of which is catalyzed by an acid and a monomer the polymerization of which is catalyzed by a base.

34. The tracer according to claim 33 in which the coating is the pruduct of furfuryl alcohol formaldehyde, furfural phenol-formaldehyde, phenol-furfural, phenol-furfuryl alcohol, furfural-acetone, urea-formaldehyde, urea-formaldehyde-furfuryl alcohol, furfural-furfuryl alcohol-phenol, analine-furfural, melamine-formaldehyde, tetrahydrofurfuryl alcohol and melamine-furfural, or any combination thereof.

35. The tracer according to claim 34 in which the core is an ion exchange resin.

36. The tracer according to claim 33 in which the core has ions selected from the group consisting of H+ and $OH^-$ ions.

37. The preparation of claim 1 in which the cores are suspended in the liquid carrier.

38. An injectable preparation for use in making circulatory system measurements comprising cores of ion exchange resin having a polymeric coating in a physiologically acceptable liquid carrier, said ion exchange resin being selected from the group consisting of a cationic exchange resin having both radioactive cations and H+ ions and an anionic exchange resin having both radioactive anions and $OH^-$ anions, and said polymeric coating comprising a polymer selected from the group consisting of a polymer, the polymerization of which is catalyzed by H+ cations, and a polymer the polymerization of which is catalyzed by $OH^-$ anions.

39. A particle comprising a core of ion exchange resin having a polymer coating thereon, said ion exchange resin being selected from the group consisting of a cationic exchange resin having both radioactive cations and H+ cations and an anionic exchange resin having both radioactive anions and $OH^{31}$ anions and said polymeric coating comprising a polymer of a monomer selected from the group consisting of a monomer, the polymerization of which is catalyzed by H+ cations, and a monomer, the polymerization of which is catalyzed by $OH^-$ anions.

40. A method of making tracer particles coated with a polymer comprising contacting cores of an ion exchange resin with a monomer of said polymer, said ion exchange resin being selected from the group consisting of a cationic exchange resin having both radioactive cations and $H^+$ cations and an anionic exchange resin having both radioactive anions and $OH^-$ anions, said monomer being selected from the group consisting of a monomer, the polymerization of which is catalyzed by $H^+$ cations, and a monomer, the polymerization of which is catalyzed by $OH^-$ anions.

* * * * *

UNITED STATES PATENT AND TRADEMARK OFFICE

CERTIFICATE OF CORRECTION

PATENT NO. : 4,107,283

DATED : Aug. 15, 1978

INVENTOR(S) : Frederick P. Pratt and David L. Gagnon

It is certified that error appears in the above-identified patent and that said Letters Patent are hereby corrected as shown below:

Col 2, line 9, change "H+" to --$H^+$--.

Col. 2, line 28, change "in" to --, on --.

Col. 2, line 63, change "or" , second occurrence to -- of --.

Col. 3, line 46, change "through" to --though--.

Col. 4, line 28, change "of" (1st occurrence) to --for--.

Col. 4, line 45, change "H+" to --$H^+$--.

Col. 5, line 7, after "accomplish" add --this,-- and change "ions" to --ion--.

Col. 5, line 68, change "means" to --mean--.

Col. 8, line 21, change "$NA^{30}$" to --Na-- and change "(NoH+)" to --(no $H^+$)--.

Col. 9, line 19, change "furfural" to --furfuryl alcohol--.

Col. 9, line 54, change "furfural" to --furfuryl alcohol--.

UNITED STATES PATENT AND TRADEMARK OFFICE

CERTIFICATE OF CORRECTION

PATENT NO. : 4,107,283

DATED : Aug. 15, 1978

INVENTOR(S) : Frederick P. Pratt and David L. Gagnon

It is certified that error appears in the above-identified patent and that said Letters Patent are hereby corrected as shown below:

Col. 9, line 18 change "OH-" to --$OH^-$--.

Col. 9, line 31, change "$NA^+$" to --$Na^+$--.

Col. 9, line 47, change "Na+" to --$Na^+$--.

Claim 1, lines 4 and 5, delete "and a physiologically acceptable liquid carrier therefor".

Claim 22, lines 4 and 7, change "H+" to --$H^+$--.

Claim 27, line 2, change "H+" to --$H^+$--.

Claim 36, line 2, change "H+" to --$H^+$--.

Claim 39, lines 5 and 9, change "H+" to --$H^+$--; and line 6, change "$OH^{31}$" to --$OH^-$--.

Claim 38, lines 7 and 11, change "H+" to --$H^+$--.

Signed and Sealed this

*Twenty-sixth* Day of *June 1979*

[SEAL]

*Attest:*

RUTH C. MASON
*Attesting Officer*

DONALD W. BANNER
*Commissioner of Patents and Trademarks*